US008324189B2

(12) United States Patent  
Galli et al.

(10) Patent No.: US 8,324,189 B2
(45) Date of Patent: Dec. 4, 2012

(54) USE OF ZOLENDRONATE FOR THE MANUFACTURE OF A MEDICAMENT FOR THE TREATMENT OF BONE METABOLISM DISEASES

(75) Inventors: Bruno Galli, Seltisberg (CH); Horst F Schran, Morristown, NJ (US); John J Seaman, New Hope, PA (US)

(73) Assignee: Novartis Pharmaceuticals Corporation, East Hanover, NJ (US)

( * ) Notice: Subject to any disclaimer, the term of this patent is extended or adjusted under 35 U.S.C. 154(b) by 1481 days.

(21) Appl. No.: 11/594,410

(22) Filed: Nov. 8, 2006

(65) Prior Publication Data

US 2007/0054885 A1 Mar. 8, 2007

Related U.S. Application Data

(63) Continuation of application No. 10/276,623, filed as application No. PCT/US01/14886 on May 9, 2001, now abandoned.

(51) Int. Cl.
  A61K 31/675 (2006.01)
  A61K 31/66 (2006.01)
(52) U.S. Cl. ............... 514/94; 514/102; 514/108
(58) Field of Classification Search .......... 514/102, 514/108, 94
  See application file for complete search history.

(56) References Cited

FOREIGN PATENT DOCUMENTS
WO WO 01/89494 11/2001

OTHER PUBLICATIONS

Major et al. Journal of Clinical Oncology, vol. 19, No. 2(Jan. 15, 2001) pp. 558-567.*
Berenson, J.R. et al., "A phase I dose-ranging trial of monthly infusions of zoledronic acid for the treatment of osteolytic bone metastases," Clinical Cancer Research, vol. 7(3), pp. 478-485 (2001).
Berenson, J.R. et al., "Zoledronic acid reduces skeletal-related events in patients with osteolytic metastases: A double-blind, randomized dose-response study," Cancer, vol. 91(7), pp. 1191-1200 (2001).
Body, J.J., "Clinical research update: Zoledronate," Cancer, vol. 80(8), pp. 1699-1701 (1997).
Lipton A. et al., "Phase II trial of zoledronate vs. pamidronate in multiple myeloma and breast cancer," Cancer Investigation, vol. 18(1), pp. 68-69 (2000).
Buckler H. et al., "Single infusion of zoledronate in Paget's disease of bone: A placebo-controlled, dose-ranging study," Bone, vol. 24(5), pp. 81S-85S (1999).
Man Z. and Otero A.B., Osteoporosis International, vol. 6, Suppl. 1, Jan. 1996, Poster session abstracts, p. 258.
Publication of Swiss marketing approval for Zometa 4 mg. Lyophilisat in the KIS Monatsbericht Nov. 2000.
Approved Swiss Label, Summary of Product Characteristics for Zometa , English Translation, 2000.
Zoledronate Disodium, Treatment of Tumor-Induced Hypercalcemia Angiogenesis Inhibitor, Drugs of the Future, 25(3), 259-268, 2000.
Green J.R. et al., Pharmacology & Toxicology, vol. 80, pp. 225-230, 1997.
Lipton, A et al., "CGP 42446-Phase I Study of a New Bisphosphonate in Patients with Osteolytic Bone Metastases", Euro Journal Cancer, 31A Suppl S197, Poster, 1995.
Zelenakas, K et al., "A Double-Blind Placebo-Controlled Trial Using Intravenous CGP-42446 in Patients with Paget's Disease of Bone", Bone, vol. 17, No. 6. pp. 597-618, Dec. 1995.
Schaffer, V. et al., "A Double Blind Placebo-Controlled Trial Using Intravenous Zoledronate (CGP-42446) in Patients with Paget's Disease of Bone", Journal of Bone and Mineral Research, vol. 11, Supp. 1, p. M766-M766, Aug. 1996.
Rosen, LS et al., "Phase I Trial of Zoledronate (CGP 42446), A New Bisphosphonate, in Patients with Osteolytic Bone Lesions", ASCO, Abstract No. 1570, 1996.
Lipton, A et al., "Phase I Study of Zoledronate (CGP 42446) in Patients with Osteolytic Bone Metastases", ESMO Congress Secretariat, Poster Paper No. 639P Meeting info: 9640175: 21$^{st}$ Congress of the European Society for Medical Oncology (9640175), Vienna Austria, Nov. 1996.
Berensen, JR. et al., Phase I Clinical Study of a New Bisphosphonate, Zoledronate (CGP-42446), In Patients with Osteolytic Bone Metastases, Blood, Supl 1; 88:10, 586a, 1998.
Schaffer, A.V. et al., "A Double Blind Placebo-Controlled Trial Using Intravenous Zoledronate (CGP 42446) in Parents with Paget's Disease of Bone", TRMP, 11 Suppl 1, S373, 1996.
Body, J.J. et al., "A Dose Finding Study of Zoledronate Intravenous Infusion in Patients with Tumour Induced Hypercalcaemia". JBMR, 11, suppl 1, p. 485, 1996.
Lipton, A. et al., "The Effects of the Bisphosphonate, Zoledronate, when Administered a Short Intravenous Infusion in Patients with Bone Metastases: A Phase I Study", Proc. Am. Soc. Clin. Oncol., vol. 16, 33 meet., 240a, 1997.
Lipton, A. "et al. Zoledronate: A New, More Potent Bisphosphonate", Bone, 22/3, suppl, 595, 1998.
Body, J.J. et al., "Zoledronate in Tumor-Induced Hypercalcemie: A Dose-Finding Study", Bone, 22/3, abstract B36, 1998.
Ali, F.J. et al., "Safety of Longterm Use of Bisphosphonates in Cancer Patients",ASCO Annuai Meeting, abstract No. 168, 1998.
Lipton, A. et al., Phase II Study of the Bisphosphonate Zoledronate in Patients with Osteolytic Lesions. Proceedings of the Second International Conference on Cancer Induced Diseases, Davos, Switzerland 1999:39, Abstract 48.
Hupkes, M. et al., "Zoledronate, a New 3$^{rd}$ Generation Bisphosphonate" Implications for Nursing Practice, Euro Journal of Cancer, Issue 35, suppl 4, Abstract 152, 1999.
Lipton, A et al., "Phase 2 Trial of Zoledronate vs Pamidronate in Multiple Myeloma and Breast Cancer", Euro Journal of Cancer 35, Suppl. 4.S360, 1999.
Saeki T. et al., "Zoledronate (ZOL): Phase I and Pharmacokinetics (PK):Pharmacodynamics(PD) Study in Cancer Patients", Bone vol. 26, No. 3, Supplement Mar. 2000:27S-42S.
Berenson, J.R. et al., "Population Pharmacokinetics (PK) of Zometa", Proc ASCO 2000, 19; 209a,meeting.

(Continued)

Primary Examiner — Jennifer M Kim
(74) Attorney, Agent, or Firm — Jennifer Chapman

(57) ABSTRACT

A method of intravenously administering a bisphosphonate to a patient in need of bisphosphonate treatment comprising intravenously administering 4 mg of 2-(imidazol-1yl)-1-hydroxyethane-1,1-diphosphonic acid (zoledronic acid) or a pharmaceutically acceptable salt thereof over a period of 15 minutes to a patient in need of said treatment.

32 Claims, 1 Drawing Sheet

OTHER PUBLICATIONS

Major, P. et al., "Zoledronic Acid is Superior to Pamidronate in the Treatment of Tumor-Induced Hypercalcemia: A Pooled Analysis", Proc ASCO 2000, 19: 605A.

Lipton, A. et al., "Phase 2 trial of Zoledronate vs Pamidronate in Multiple Myeloma and Breast Cancer", Euro Journal of Cancer, vol. 35, suppl 4, S360, 1999.

Berenson, J. et al., "Phase I Study of Zoledronate Administered as a 30-60 Second Intravenous Infusion in Cancer Patients", Cancer, vol. 88 (12), p. 3101, Jun. 15. 2000.

Berenson, J. et al., "Phase II Trial of Zoledronate versus Pamidronate in Multiple Myeloma and Breast Carcinoma Patients with Osteolytic Lesions", Cancer Supplement, Jun. 15, 2000, vol. 88, No. 12, pp. 3102.

Lipton, A. et al., "Phase I Study of Zoledronate in Cancer Patients with Lytic Bone Disease", Cancer, vol. 88(12), p. 3105, 2000.

Approved Label Canada, Aug. 2000.

Fleisch, "Bisphosphonates: Mechanisms of Action", Endocrine Reviews, 19(1):80-100 (1998).

"Guidelines for the use of Zoledronic Acid for the Treatment of Tumor Induced Hypercalcemia," QEII Health Sciences Centre/Cancer Care Nova Scotia, pp. 1-9 (Mar. 2001).

Arden-Cordone, M., et al., "Antiresorptive Effect of a Single Infusion of Microgram Quantities of Zoledronate in Paget's Disease of Bone," Calcified Tissue International, pp. 415-418 (1997).

Kanis, J. A., et al., "Effects of Intravenous Etidronate Disodium on Skeletal and Calcium Metabolism," The American Journal of Medicine, vol. 82 (Supp. 2A), pp. 55-70 (1987).

Mian, M., et al., "Tolerability and Safety of Clodronate Therapy in Bone Disorders," Int. J. Clin. Pharm. Res, XI(2), pp. 107-114 (1991).

\* cited by examiner

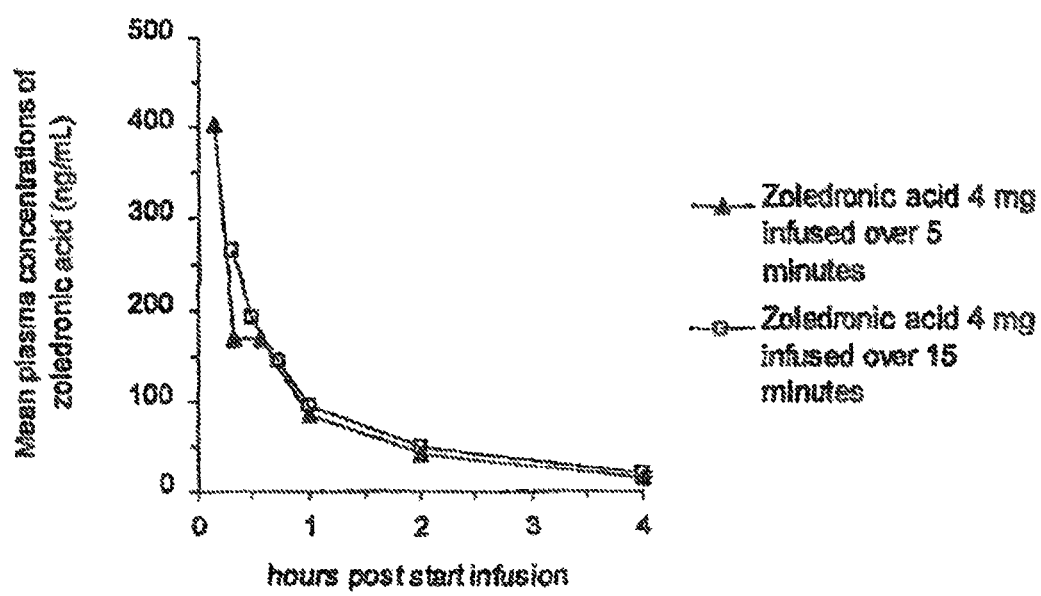

USE OF ZOLENDRONATE FOR THE MANUFACTURE OF A MEDICAMENT FOR THE TREATMENT OF BONE METABOLISM DISEASES

This application is a continuation of U.S. application Ser. No. 10/276,623, filed Jan. 21, 2003, which is a 371 of International Application No. PCT/US01/14886, filed May 9, 2001.

The present invention relates to a method of intravenously administering a bisphosphonate, specifically 2-imidazol-1yl)-1-hydroxyethane-1,1-diphosphonic acid (zoledronic acid) to a patient in need of bisphosphonate treatment.

Bisphosphonates are widely used to inhibit osteoclast activity in a variety of both benign and malignant diseases that involve excessive or inappropriate bone resorption. These pyrophosphate analogues not only reduce the occurrence of skeletal related events but they also provide patients with clinical benefit and improved survival. Bisphosphonates are able to prevent bone resorption in vivo; the therapeutic efficacy of bisphosphonates has been demonstrated in the treatment of osteoporosis, osteopenia, Paget's disease of bone, tumour-induced hypercalcemia (TIH) and, more recently, bone metastases (BM) and multiple myeloma (MM) (for review see Fleisch H 1997 Bisphosphonates clinical. In Bisphosphonates in Bone Disease, From the Laboratory to the Patient. Eds: The Parthenon Publishing Group, New York/London pp 68-163).

Recently, it has been reported that bisphosphonate (clodronate, etidronate, alendronate and pamidronate) administration has a favourable effect on bone pain in patients with metastatic prostate cancer carcinoma (Silvio Adami, Cancer 1997; 80: 1674-79). Recently, it has also been reported that bisphosphonates inhibit breast and prostate carcinoma cell adhesion to bone in vitro (Boissier et al., Cancer Res; 57: 3890-3894, 1997) and further that pre-treatment of breast and carcinoma cells with bisphosphonates inhibited tumour cell invasion via a direct action on the tumour cells. Yet more recently, it has been reported that in vitro treatment of prostate cancer cell lines with zoledronic acid significantly reduced the growth of the cell lines (Brown et al. Effects of Zoledronate on Prostate Cancer Cells, ASBMR 2000; Lee et al., Bisphosphonate Treatment Inhibits the Growth of Prostate Cancer Cells, Cancer Research, 2000/2001); whereas no significant decrease in tumour volume was detected for subcutaneous prostate cancer cell line tumours treated with zoledronic acid (Corey et al., Effects of Zoledronic Acid on Prostate Cancer in Vitro and in Vivo, Amer. Assoc. Cancer Res. Submitted October 2000).

Additionally, it has now been shown in a double blind, placebo-controlled clinical study that zoledronic acid (zoledronate) demonstrates a statistically significant efficacy benefit over placebo in the treatment of bone metastases in prostate cancer patients and that bisphosphonates may also be employed more generally for the treatment of osteoblastic (osteosclerotic) metastases, in particular osteoblastic bone metastases, such as the osteoblastic metastases associated with prostate cancer and similar malignant diseases in mammals.

1-hydroxy-2(1H-imidazol-1-yl)-phosphono-ethyl phosphonic acid (zoledronic acid, zoledronate) is a third generation bisphosphonate compound. In animal models zoledronic acid shows high affinity to the mineralised bone matrix and inhibits osteoclastic bone resorption more effectively than earlier generation bisphosphonates, at doses that do not affect bone formation and mineralization and have no appreciable impact on renal function. This results in an improved ratio of antiresorptive versus renal effects (Green et al., 1994; Green et al., 1997). Zoledronic acid (ZOMETA™) is currently under regulatory review for the treatment of tumor-induced hypercalcemia (TIH) on the basis of safety and efficacy data in a dose finding study (Vigneron et al., 1995) and two pivotal clinical trials (Mull et al., 1999; O'Neill et al., 1999), as well as supporting safety data from several other studies in cancer patients with bone metastases (van Valen et al., 1999; Goas et al., 1999; Borg et al., 1999). The clinical studies demonstrate that the pharmacological action of zoledronic acid in reducing osteoclastic hyperactivity results in an effective clinical inhibition of bone resorption and calcium release into blood in TIH patients.

BRIEF DESCRIPTION OF THE DRAWINGS

FIG. 1. Plasma concentrations in patients after 4 mg zoledronic acid infused over 5 minutes and 15 minutes (mean data for n=5 patients in 4 mg/5 min group, n=7 patients in 4 mg/15 min group, study 503 [2]

It has been found that an intravenously administered 4 mg dose of zoledronic acid infused over an interval of approximately 15 minutes showed 1) improved clinical practicality, 2) potentially more reproducible infusion rate when using 100 ml over 15 min vs. lower volume infused over shorter period, 3) shows comparable efficacy to the current standard treatment, Aredia® (disodium pamidronate) 90 mg dosed over a period of 2-4 hours, and 4) 4 mg/15 minutes shows improved renal safety versus 4 mg/5 minutes and higher zoledronic acid dose/15 minutes. Thus in one embodiment, the invention is directed to a method of administering 2-(imidazol-1yl)-1-hydroxyethane-1,1-diphosphonic acid (zoledronic acid, zoledronate) to a patient in need of bisphosphonate treatment comprising intravenously administering 4 mg of 2-(imidazol-1-yl)-1-hydroxyethane-1,1-diphosphonic acid or a pharmaceutically acceptable salt thereof over a period of 15 minutes to a patient in need of said treatment.

In another embodiment, the present invention relates to a method of treatment of bone metabolism diseases, e.g., tumour induced hypercalcemia (TIH), prosthesis loosening, treatment or reversal of angiogenesis associated with pathological conditions, e.g. tumour angiogenesis, said method comprising intravenously administering 4 mg of 2-(imidazol-1-yl)-1-hydroxyethane-1,1-diphosphonic acid or a pharmaceutically acceptable salt thereof over a period of 15 minutes to a patient in need of said treatment.

In a further embodiment, the present invention relates to a method of treatment of bone metastases, said method comprising intravenously administering 4 mg of 2-(imidazol-1yl)-hydroxyethane-1,1-diphosphonic acid or a pharmaceutically acceptable salt thereof over a period of 15 minutes to a patient in need of said treatment.

In a still further embodiment, the present invention relates to a method of treatment or prevention of multiple myeloma, said method comprising intravenously administering 4 mg of 2-(imidazol-1yl)-1-hydroxyethane-1,1-diphosphonic acid or a pharmaceutically acceptable salt thereof over a period of 15 minutes to a patient in need of said treatment.

In the present description the terms "treatment" or "treat" refer to both prophylactic or preventative treatment as well as curative or disease modifying treatment, including treatment of patients at risk of developing TIH, BM, or MM or suspected to have contracted the disease, e.g. TIH, as well as patients who are ill or have been diagnosed as suffering from a particular disease or medical condition treatable with bisphosphonates.

Zoledronic acid, chemically designated as 1-hydroxy-2-(imidazol-1-yl)ethane-1,1-diphosphonic acid having the structure

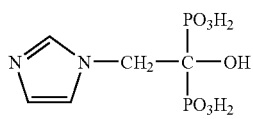

is known and can be prepared as described e.g. in U.S. Pat. No. 4,939,130 (see also U.S. Pat. Nos. 4,777,163 and 4,687,767), the contents of the latter three patents are hereby incorporated by reference.

Pharmaceutically acceptable salts of 1-hydroxy-2-(imidazol-1-yl)ethane-1,1-diphosphonic acid are preferably salts with bases, conveniently metal salts derived from groups Ia, Ib, IIa and IIb of the Periodic Table of the Elements, including alkali metal salts, e.g. potassium and especially sodium salts, or alkaline earth metal salts, preferably calcium or magnesium salts, and also ammonium salts with ammonia or organic amines.

Especially preferred pharmaceutically acceptable salts are those where one, two, three or four, in particular one or two, of the acidic hydrogens of the bisphosphonic acid are replaced by a pharmaceutically acceptable cation, in particular sodium, potassium or ammonium, in first instance sodium.

A very preferred group of pharmaceutically acceptable salts is characterised by having one acidic hydrogen and one pharmaceutically acceptable cation, especially sodium, in each of the phosphonic acid groups.

Zoledronic acid can also be used in the form of its hydrates or it may include other solvents used for crystallisation.

The zoledronic acid is preferably administered in the form of pharmaceutical compositions that contain the 4 mg therapeutically effective amount optionally together with or in admixture with inorganic or organic, solid or liquid, pharmaceutically acceptable carriers which are suitable for intravenous administration.

The method according to the instant invention is for the intravenous administration of zoledronic acid.

The intravenous formulations used in the methods of the instant invention are injectable fluids which are preferably isotonic aqueous solutions which can be prepared before use by methods well known in the art, for example from lyophilised preparations which contain active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers. Preferred intravenous infusion solutions are those containing 4 mg of zoledronic acid per unit dose in an infusion solution volume of from about 5 up to about 200 ml, preferably from about 50 to about 100 ml and more preferably about 100 ml for infusion over a period of about 15 minutes plus or minus up to about 45 seconds.

Preferably, the compositions of the invention comprise a buffering agent. The type and amount of buffering agent may be selected in order to obtain a pH in the range of from 5 to 7, e.g., pH 5.9, when the composition of the invention is dissolved, e.g., in water. We have found that stability is best at these pH values. The pH may also be adjusted by using a basic solution, e.g., a sodium hydroxide solution. As a preferred buffering agent one may use trisodium citrate.

It is also preferred that the compositions of the invention comprise a bulking agent which preferably also acts as an isotonising agent. Preferably, the bulking/isotonising agent is chemically inert, has a low hygroscopicity and good bulking properties. The amount of bulking/isotonising may be selected in order to obtain an isotonic solution when the composition of the invention is dissolved. For example the weight ratio of Zoledronic acid to the bulking/isotonising agent is in the range of from 1:5 to 1:4000, e.g., 1:10 to 1:3000, e.g., 1:20 to 1:2500, e.g., 1:30 to 1:1000, e.g., 1:40 to 1:500, e.g., 1:50 to 1:150. As a preferred bulking/isotonising agent one may use mannitol.

The intravenous solution may be obtained by dissolving a pharmaceutical composition as described above into an appropriate amount of a biocompatible water-based solvent, water or saline for parenteral administration.

For treatment of tumor induced hypercalcemia, zoledronic acid is preferably administered one time in most patients. Repeat dosing, administered no sooner than 7 days post initial treatment, normally limited to one occurrence, may be used for improved control of the hypercalcemia. For the treatment and prevention of bone metastases, long-term administration of zoledronic acid is generally administered at 3 to 4-week intervals and at monthly intervals for patients with multiple myeloma although this can be more or less frequent depending upon individual circumstances. For example in one standard double blind clinical trial for Tumour Induced Hypercalcemia, 4 mg and 8 mg equivalents of Zoledronic acid delivered as a sodium salt of zoledronic acid are diluted with 50 ml of an intravenous infusion solution (composition of the invention) and are delivered to a patient over a 15 minutes period once a day. Patients are retreated with an 8 mg dose if desired. Preferably, a minimum of 7 days, e.g., 14 days, should elapse before re-treatment to allow for full response to the initial dose.

The compositions of the invention may be prepared as follows. The required amount of isotonising agent is dissolved in, e.g., 50 to 90%, of the total amount of biocompatible water-based solvent or water. Zoledronic acid is then suspended and dissolved by adding a solution of the buffering agent. After complete dissolution the pH-value is adjusted to the desired range with the required amount of buffering agent. The solution is then made up to the final volume with biocompatible water-based solvent or water for parenteral use. Then the process is continued under aseptic conditions. The solution is sterilised and filled into 4 to 10 ml vials. In plastic vials, the solutions may be stored for a long-term period.

Before storage, the content of the vials may also be dried, e.g., freeze-dried, according to a pre-programmed cycle. When the cycle is complete, the vials are stoppered after flushing with a gas, e.g., nitrogen or carbon dioxide, within a chamber. The vials are sealed, e.g., with aluminium caps, outside the sterile area. The lyophilisate may then be used by re-dissolving the content of the vials into a solvent suitable for intravenous administration, e.g. saline.

The present invention is illustrated by the following examples.

EXAMPLE 1

In a stainless steel kettle the required amount of mannitol is dissolved by stirring and under nitrogen flushing in approximately 70% of the total amount of water for injection. Zoledronic acid is suspended and dissolved by adding a 10% trisodium citrate solution. After complete dissolution the pH-value is adjusted with 10% trisodium citrate solution to 5.9-6.1. The solution is then made up to the final volume with water for injection. The following procedure is carried out under aseptic conditions (in a grade A clean area): The solution is passed through a sterile membrane filter (0.22 micrometers pore size), and filled into 6 ml vials with a filling weight of 1.945 g (including an overfill of 3% of the solution to be lyophilised in order to compensate for the amount of reconstituted solution remaining in the vial after withdrawal). The overfill is selected according to USP. The vials are freeze-dried according to the following cycle:

| Step | Time [min.] | Temperature [° C.] | Pressure [mbar] |
|---|---|---|---|
| Begin freezing | 30 min. | −20° C. | — |
| Freezing | 90 min. | −45° C. | — |
| Freezing equilibration time | 150 min. | −45° C. | — |
| Begin primary drying | 35 min. | −10° C. | 1500 |
| Primary drying | 85 min. | 13° C. | 1500 |
| Primary drying | 480 min. | 13° C. | 1500 |
| Begin secondary drying | 30 min. | 30° C. | 420 |
| Secondary drying | 300 min. | 30° C. | 420 |
| Cooling down | 30 min. | 20° C. | 420 |
| End of cycle | 5 min. | 20° C. | 420 |

When the cycle is complete, the vials are stoppered after flushing with nitrogen within the chamber. The vials are sealed with aluminium caps outside the sterile area (under LF). A solution for intravenous injection may be reconstituted by adding 5 ml of sterile water for injection USP to each vial. This dose is further diluted in 50 ml of sterile 0.9% Sodium Chloride, USP, or 5% Dextrose Injection, USP. If not used immediately, for microbiological integrity, the solution is refrigerated at, e.g., 36°-46° F. (2-8° C.). The total time between reconstitution, dilution, storage in the refrigerator and end of administration does not preferably exceed 24 hours.

EXAMPLES 2

According to a similar processing as in example 1 the following composition may be obtained.

| Compositions | |
|---|---|
| Zoledronic acid | 4 mg |
| Mannitol, pyrogen-free | 220.0 mg |
| Trisodium citrate | up to pH 5.9 |
| Sodium hydroxide | — |
| Water for injection | up to 1.8 ml |

EXAMPLE 9

An 8 mg composition is prepared similarly as in example 1. The type and amounts of components are the same as for the 4 mg composition (example 7). Only amount of Zoledronic acid and trisodium citrate is doubled while the amount of mannitol is reduced down to 150 mg.
The Composition of Example 2 may be freeze dried and re-constituted as described in Example 1.
4 mg zoledronic acid is reconstituted in 100 ml of infusion solution. The solution is infused over a period of 15 minutes. This corresponds to an infusion rate of drug of 4 mg/15 minutes=0.27 mg/minute=1 micromole/minute. The 4 mg dose, infused over 15 minutes, represents a more practical alternative to other bisphosphonate drugs, which are infused over a considerably longer period of time and at a higher infusion rate in terms of mass per unit time (mg/minute) and number of molecules per unit time (micromoles/minute), as tabulated below:

| | Bisphosphonate Drug | |
|---|---|---|
| | zoledronic acid | pamidronate |
| Clinical dose (mg) | 4 | 90 |
| Infusion time (minutes) specified in label | 15 | 120 |
| Infusion rate | | |
| mg/minute | 0.27 | 0.75 |
| micromoles/minute | 1 | 2 |

1. The volume of 100 ml containing 4 mg zoledronic acid is infused over 15 minutes as an intravenous drip, which allows the drug to be administered at a uniform and precise rate. Clinical use of shorter infusion times of zoledronic acid, for example as an intravenous push of 5 minutes [Major P, Lortholary A, Hon J,. et al., Zoledronic acid is superior to pamidronate in the treatment of hypercalcemia of malignancy: a pooled analysis of two randomized, controlled clinical trials, J Clin Oncol 2001; 19: 558-567], may result in more variable infusion rates. Changing the infusion rate impacts the peak plasma concentrations achieved, as demonstrated in a pharmacokinetic study of zoledronic acid in cancer patients with bone metastases. Relevant data are shown in FIG. 1.

The pharmacokinetic parameters derived from the individual patients' plasma concentration versus time curves, and urinary excretion of drug are tabulated below. Differences in mean Cmax (maximum observed zoledronic acid concentration, at end of infusion) were statistically significant. Differences in AUC (area under zoledronic acid concentration versus time curve) and Ae (amount of drug excreted in urine) were not significant.

| | Zoledronic acid 4 mg infused over 15 minutes (n = 7) | Zoledronic acid 4 mg infused over 5 minutes (n = 5) |
|---|---|---|
| Cmax (ng/ml) | 264 ± 86 | 403 ± 118 |
| AUC 0-24 h (ngxh/ml) | 420 ± 218 | 378 ± 116 |
| Ae 0-24 h (% of dose) | 37.4 ± 17.0 | 38.7 ± 6.34 |

The 4 mg dose of zoledronic acid has been determined to be clinically effective in several controlled trials in cancer patients, with placebo or the bisphosphonate pamidronate as comparator. Pertinent data attesting to zoledronic acid showing comparable efficacy to pamidronate and superior efficacy against placebo are summarized below.

| | Percentage of patients showing a skeletal related adverse event | | |
|---|---|---|---|
| | Zoledronic acid 4 mg | Comparator: Placebo or pamidronate | Statistical significance |
| Study 10: | | | |
| breast cancer patients | 42% | 47% | P > 0.05 |
| multiple myeloma patients | 47% | 49% | P > 0.05 |
| Study 11: | | | |
| hypercalcemic lung cancer patients | 42% | 48% | P = 0.036 |
| hypercalcemic patients with other solid tumors | 33% | 46% | P = 0.047 |
| Study 39: | | | |
| prostate cancer patients | 33% | 44% | P = 0.021 |

The dose of 4 mg zoledronic acid infused over 15 minutes offers a safety advantage in terms of renal tolerability over the shorter infusion time of 5 minutes. The lower incidence of renal adverse events with zoledronic acid infused over 15 minutes versus 5 minutes is summarized below. Renal adverse events are defined as increases in a patient's serum creatinine over baseline, by $\leq 0.5$ mg/dL if baseline <1.4 mg/dL, by $\leq 1$ mg/dL if baseline $\leq 1.4$ mg/dL, by $\leq 2$-fold irrespective of baseline value.

| | zoledronic acid 4 mg | |
|---|---|---|
| | 15 minutes infusion | 5 minutes infusion |
| Study 10: breast cancer and multiple myeloma patients | 24/272 patients 8.8% | 36/272 patients 13.2% |
| Study 11: lung cancer patients | 18/165 patients 10.9% | 10/61 patients 16.4% |
| Study 39: prostate cancer patients | 14/78 patients 15.2% | 22/111 patients 19.8% |

Zoledronic acid 4 mg infused over 15 minutes showed similar renal tolerability compared to pamidronate 90 mg infused over 2 hours, 8.8% versus 8.2%, respectively.

4 mg of zoledronic acid infused over 15 minutes versus higher doses of zoledronic acid, 8 mg and 16 mg results in improved renal safety without, surprisingly, losing clinical efficacy.

In summary, 4 mg zoledronic acid infused in a 100 mL volume over 15 minutes offers an input rate of drug into the patients' systemic circulation of 1 micromole per minute, which can be precisely administered and is considerably lower than the infusion rate used for other bisphosphonate drugs. The shorter duration of the infusion, 15 minutes for zoledronic acid versus 2 hours for pamidronate, offers a greater degree of flexibility and practicality in the clinical setting. The clinical studies attest to a clinical benefit in the choice of zoledronic acid 4 mg dose infused over 15 minutes in terms of improved renal tolerability versus a shorter infusion period of 5 minutes, but without impacting clinical efficacy, which is comparable to the current standard therapy pamidronate, and superior to placebo.

We claim:

1. A method of treatment of bone metabolism diseases, said method comprising intravenous administration of 4 mg of 2-(imidazol-1yl)-1-hydroxyethane-1,1-diphosphonic acid or a pharmaceutically acceptable salt thereof in an infusion solution volume of from about 5 up to about 200 ml over a period of 15 minutes to a patient in need of said treatment, wherein said intravenous administration improves renal safety.

2. The method according to claim 1, wherein said bone metabolism disease is tumour induced hypercalcemia.

3. The method according to claim 1, wherein said infusion volume is from about 50 to about 100 ml.

4. The method according to claim 1, wherein said infusion volume is about 100 ml.

5. The method according to claim 1, wherein the 2(imidazol-1yl)-1-hydroxyethane-1,1-diphosphonic acid is in the form of a pharmaceutically acceptable salt having one acidic hydrogen and one pharmaceutically acceptable cation in each of the phosphonic acid groups.

6. The method according to claim 5, wherein said pharmaceutically acceptable cation is sodium.

7. A method of treatment of bone metastases, said method comprising intravenous administration of 4 mg of 2-(imidazol-1yl)-1-hydroxyethane-1,1-diphosphonic acid or a pharmaceutically acceptable salt thereof in an infusion solution volume of from about 5 up to about 200 ml over a period of 15 minutes to a patient in need of said treatment, wherein said intravenous administration improves renal safety.

8. The method according to claim 7, wherein said infusion volume is from about 50 to about 100 ml.

9. The method according to claim 7, wherein said infusion volume is about 100 ml.

10. The method according to claim 7, wherein the 2-(imidazol-1yl)-1-hydroxyethane-1,1-diphosphonic acid is in the form of a pharmaceutically acceptable salt having one acidic hydrogen and one pharmaceutically acceptable cation in each of the phosphonic acid groups.

11. The method according to claim 10, wherein said pharmaceutically acceptable cation is sodium.

12. A method of treatment of multiple myeloma, said method comprising intravenous administration of 4 mg of 2-(imidazol-1yl)-1-hydroxyethane-1,1-diphosphonic acid or a pharmaceutically acceptable salt thereof in an infusion solution volume of from about 5 up to about 200 ml over a period of 15 minutes to a patient in need of said treatment, wherein the intravenous administration improves renal safety.

13. The method according to claim 12, wherein said infusion volume is from about 50 to abut 100 ml.

14. The method according to claim 12, wherein said infusion volume is about 100 ml.

15. The method according to claim 12, wherein the 2-(imidazol-1yl)-1-hydroxyethane-1,1-diphosphonic acid is in the form of a pharmaceutically acceptable salt having one acidic hydrogen and one pharmaceutically acceptable cation in each of the phosphonic acid groups.

16. The method according to claim 15, wherein said pharmaceutically acceptable cation is sodium.

17. A method of treatment of bone metabolism diseases, said method comprising intravenous administration of 4 mg of 2-(imidazol-1yl)-1-hydroxyethane-1,1-diphosphonic acid or a pharmaceutically acceptable salt thereof in an infusion solution volume of from about 5 up to about 200 ml over a period of 15 minutes to a patient in need of said treatment, wherein said intravenous administration reduces incidence of renal toxicity.

18. The method according to claim 17, wherein said bone metabolism disease is tumour induced hypercalcemia.

19. The method according to claim 17, wherein said infusion volume is from about 50 to about 100 ml.

20. The method according to claim 17, wherein said infusion volume is about 100 ml.

21. The method according to claim 17, wherein the 2(imidazol-1yl)-1-hydroxyethane-1,1-diphosphonic acid is in the form of a pharmaceutically acceptable salt having one acidic hydrogen and one pharmaceutically acceptable cation in each of the phosphonic acid groups.

22. The method according to claim 21, wherein said pharmaceutically acceptable cation is sodium.

23. A method of treatment of bone metastases, said method comprising intravenous administration of 4 mg of 2-(imidazol-1yl)-1-hydroxyethane-1,1-diphosphonic acid or a pharmaceutically acceptable salt thereof in an infusion solution volume of from about 5 up to about 200 ml over a period of 15 minutes to a patient in need of said treatment, wherein said intravenous administration reduces incidence of renal toxicity.

24. The method according to claim 23, wherein said infusion volume is from about 50 to about 100 ml.

25. The method according to claim 23, wherein said infusion volume is about 100 ml.

26. The method according to claim 23, wherein the 2-(imidazol-1yl)-1-hydroxyethane-1,1-diphosphonic acid is in the form of a pharmaceutically acceptable salt having one acidic hydrogen and one pharmaceutically acceptable cation in each of the phosphonic acid groups.

27. The method according to claim 26, wherein said pharmaceutically acceptable cation is sodium.

28. A method of treatment of multiple myeloma, said method comprising intravenous administration of 4 mg of 2-(imidazol-1yl)-1-hydroxyethane-1,1-diphosphonic acid or a pharmaceutically acceptable salt thereof in an infusion solution volume of from about 5 up to about 200 ml over a period of 15 minutes to a patient in need of said treatment, wherein the intravenous administration reduces incidence of renal toxicity.

29. The method according to claim 28 wherein said infusion volume is from about 50 to about 100 ml.

30. The method according to claim 28, wherein said infusion volume is about 100 ml.

31. The method according to claim 28, wherein the 2-(imidazol-1yl)-1-hydroxyethane-1,1-diphosphonic acid is in the form of a pharmaceutically acceptable salt having one acidic hydrogen and one pharmaceutically acceptable cation in each of the phosphonic acid groups.

32. The method according to claim 31, wherein said pharmaceutically acceptable cation is sodium.

* * * * *